United States Patent [19]

Almeida et al.

[11] 4,148,876

[45] Apr. 10, 1979

[54] BIOLOGICAL PREPARATIONS

[75] Inventors: June D. Almeida, London; David C. Edwards, Beckenham, both of England

[73] Assignee: Burroughs Wellcome Co., Research Triangle Park, N.C.

[21] Appl. No.: 882,445

[22] Filed: Mar. 1, 1978

Related U.S. Application Data

[63] Continuation-in-part of Ser. No. 727,610, Sep. 28, 1976, abandoned.

[51] Int. Cl.² .................. A61K 39/12; A61K 39/18; A61K 39/20; A61K 39/22
[52] U.S. Cl. .................................................... 424/89
[58] Field of Search .................................. 424/89–92

[56] References Cited

U.S. PATENT DOCUMENTS

| | | | |
|---|---|---|---|
| 3,887,698 | 6/1975 | McConnell et al. | 424/12 |
| 4,053,585 | 10/1977 | Allison et al. | 424/92 |

FOREIGN PATENT DOCUMENTS

| | | |
|---|---|---|
| 846681 | 3/1977 | Belgium. |
| 2249552 | 5/1973 | Fed. Rep. of Germany. |
| 73/01850 | 11/1973 | South Africa. |

OTHER PUBLICATIONS

Haywood, Am. July 1973, Symp. Neg. Strand. Viruses, Cambridge, Enc. vol. 2:923–928, Academic Press 1975.
Haywood, Am. (1974), J. Molecular Biology 83(4):427–436 (1974).
Haywood, Am. (1974) J. Molecular Biology 87(3):625–628 (1974).
Gregoriadis et al. FEBS Letters 45(1):71–74, Sep. 1974.
Mooney et al., J. Virology 15(2):225–231 (1975).
Heath et al., Biochemical Society Transactions 4(1):129–133 (1976).

*Primary Examiner*—Shep K. Rose
*Attorney, Agent, or Firm*—Donald Brown

[57] ABSTRACT

A novel antigenic preparation which comprises a plurality of microvesicles are unilamellar bodies comprising a single lipid bilayer upon the exterior surface of which is bound an antigenic protein derived from a virus and having a hydrophobic region.

12 Claims, No Drawings

BIOLOGICAL PREPARATIONS

This application is a continuation-in-part of application Ser. No. 727,610 dated Sept. 28th, 1976, now abandoned.

This invention relates to antigenic preparations.

It is known that while a variety of inactivated viruses, for example influenza virus, are good immunogens, they are also pyrogenic. Attempts to remove the pyrogenicity by purifying the immunogenic moiety of the virus have been successful but the resulting viral subunits do not provide a very active immunogen. There is therefore a need for a suitable adjuvant for such subunits and other antigenic proteins which would boost the immune response in the vaccinated host.

There is an increasing interest in the use of liposomes as carriers of drugs and enzymes and in their potential as immunological adjuvants. Liposomes consist of aqueous dispersions of concentric spheres consisting of phospholipid bilayers separated by aqueous compartments. They are essentially onion-like structures which have been fully described in the literature. They can be produced when a dried film of a phospholipid such as lecithin is shaken in the presence of a buffer.

In previous publications on the use of liposomes as carriers the drugs, enzymes or antigens are described as entrapped within the internal aqueous compartments of unilamellar or multilamellar lipid bodies. Amphipathic antigenic material (derived from bacteria) has also been described as attached to the exterior of such lipid bodies as a means of sensitization.

It has now been found that when antigenic material derived from viruses and having a hydrophobic region are bound to the outside of vesicles comprising unilamellar bodies, the antigen-vesicle complex has excellent antigenic properties when compared with either the unbound antigen or the antigen bound to the surface of multilamellar liposomes. When the viral antigen-unilamellar vesicle complex is viewed under an electron microscope the antigenic sub-units appear to be arranged in the same manner as on the parent virus particle and the antigen-vesicle combination as a whole looks similar in both shape and size to the parent pathogen particle. This is not so in the case where either the antigen is attached to multilamellar liposomes or antigens derived from pathgens other than viruses are attached to vesicles (unilamellar or multilamellar). It is this unexpected re-creation of the virus particle which it is believed gives rise to excellent antigenic properties found for the virosomes derived from unilamellar vesicles.

In order for a successful recreation of the virus the antigenic protein should be derived from a single species type virus. Each microvesicle is preferably within the size range of 40 to 100 nm, though other bodies are also within the scope of this invention, for example bodies of from 20 to 100 nm.

The antigenic protein may be derived from any suitable virus. Protective surface antigens derived from myxoviruses, such as influenza virus A, B and C, Newcastle disease virus, and parainfluenza types 1, 2, 3 and 4 as well as other viruses such as measles virus, mumps virus, cytomegalovirus and other herpes viruses and corona viruses are especially suitable.

The protein antigens are bound to the microvesicles by hydrophobic bonding, and it is an essential feature of the invention that the antigenic protein possesses a hydrophobic region.

The microvesicles may be made by any suitable lipid material, conveniently one which is itself biodegradable and non-antigenic. Conventional materials such as natural or synthetic lecithins or other phospholipids are notably useful. Other lipids may also be included such as cholesterol as a strengthener, preferably in an amount of less than 30 moles % w/w of the whole lipid composition. An optional third material to provide a positive or negative charge may also be included. Materials which provide a negative charge include phosphatidic acid, beef brain ganglioside, dicetyl phosphate, phosphatidyl serine, and phosphatidyl inositol; materials providing a positive charge are stearylamine and other primary amines.

The microvesicles may optionally encapsulate a second adjuvant such as one of the customary adjuvants known in the art.

The antigenic protein may be added to the lipid materials before or after the formation of the microvesicles, but preferably after to eliminate the possibility of the protein being entrapped within the bodies rather than being bound to the exterior surfaces.

The unilamellar microvesicles may be made by any known method, and conveniently by dissolving the lipid starting material(s) in a solvent and evaporating the solvent. The lipid layer is then dispersed with aqueous saline or a buffer (if it is intended to incorporate the protein after microvesicle formation) or with an aqueous suspension of the protein prior to microvesicle formation), and the mixture then agitated. Protein may then be added where it is not already incorporated, and the microvesicles again agitated. The period of time required to obtain unilameller microvesicles will depend upon the particular lipid used but will be at least of 15 minutes duration and in some cases as long as 2 hours.

An alternative method is to add the lipid starting material(s) to an aqueous phase, and slowly heat the mixture. It is then agitated to form the unilamellar vesicles. The aqueous phase may contain the antigenic protein or it may be added subsequently.

A further method of preparing the unilamellar microvesicles comprises the rapid injection of an ethanolic solution of phospholipid into aqueous saline or a buffer which has been previously purged with nitrogen. The resulting microvesicle preparation is then concentrated by ultra-filtration with rapid stirring under nitrogen at low pressure to avoid the formation of larger non-heterogeneous liposomes. The ethanol may be removed from the liposome fraction by dialysis or washing on an ultra-filter. The antigenic protein which is intended to be bound to the microvesicle may be present in the aqueous solution, or alternatively the microvesicle fraction obtained after ultra-filtration may be lightly sonicated with the antigenic protein.

The antigenic preparations obtained in the manner described above comprise aqueous dispersions of the microvesicles, and these may be formulated into vaccines by incorporating them in a sterilised form in sealed single dose or multi dose containers. Preservatives, stabilisers and other conventional vaccine excipients, if desired, may be included.

Vaccines so produced may be administered by the methods customarily used for the administration of the particular antigenic protein or proteins in the vaccine. This usually takes the form of nasal application, intramuscular or subcutaneous injection into the animal (including man). The dose is of course dependent upon the nature of the antigen, the recipient animal, the vaccination schedule, and the extent of adjuvenicity conferred by the preparation, and is of course at the discretion of the attendant physician or veterinary surgeon, as appropriate.

In general a dose of the vaccine may be administered as a single unit, or as a multiplicity of sub-doses over a period of time.

Accordingly the invention provides the following:
(a) an antigenic preparation comprising a plurality of unilamellar microvesicles upon the exterior surface of which a virus derived antigenic protein having a hydrophobic region is bound by hydrophobic bonding; 1
(b) a process for preparing the antigenic preparation;
(c) pharmaceutical formulations containing the antigenic preparation;
(d) method of making such pharmaceutical formulations; and
(e) a method for the prophylaxis of an infection in a mammal, including man which comprises the administration of a non-toxic, prophylactic amount of the antigenic preparation.

The following Examples are provided by way of an illustration of the present invention and should not be construed as a limitation thereof.

EXAMPLE 1

A. Preparation of Influenza Virus Subunits

Highly purified (according to the method of J.J. Skehcle and G.C. Schield, Virology, 1971, 44, 396–408) PR8 influenza virus at 12 mg. virus protein per ml. was mixed with non-ionic detergent (Nonidet NP40) to a final detergent concentration of 5% v/v and layered onto 11 ml. gradients of cesium chloride from 24–45% w/v cesium chloride (in 0.05M sodium phosphate buffer pH 7.0) with 0.3 ml. sucrose overlays. The gradients were centrifuged at 100,000 g. for three hours or more, fractionated and the fractions assayed for haemagglutinating activity. High activity fractions were pooled, vacuum dialysed against phosphate buffered saline (PBS) and layered onto a second gradient of 20–60% w/v sucrose in PBS and centrifuged at 100,000 g for 16 hours. The fractions were again assayed for haemagglutinating activity, high titres pooled and vacuum dialysed against PBS. The final solution had a protein concentration of 1.76 mg/ml and a haemagglutinating activity of approximately $10^6$ HAU/ml. For production of liposomes the subunit mixture was adjusted to a final protein concentration of 200 µg/ml.

The phosphate buffered saline (PBS) had a composition of sodium chloride 10 g/liter, potassium chloride 0.25 g/liter; potassium dihydrogen phosphate 0.25 g/liter; and disodium hydrogen phosphate 1.4375 g/liter.

B. Preparation of Microvesicles

Dicetyl phosphate (2.5 mg) and lecithin (22.5mg) were dissolved in chloroform (approximately 50 ml). The solution was evaporated to dryness on a Buchi evaporator under a slight vacuum. PBS (phosphate buffered saline) was added to the contents of the flask to provide a lipid concentration of 16.6 µM/ml and the flask was agitated manually and mechanically until the lipid was suspended in the fluid. This mixture was sonicated for 1.5 hours in an ultrasonic bath at a frequency of 50 KH$_z$.

C. To the resulting preparation was added influenza virus subunits, prepared as described in A above, to a concentration of 200 µg/ml. This mixture was then sonicated for a further 15 minutes in a ultrasonic bath at a frequency of 50 KHz.

D. Examination in the election microscope by the negative staining technique of the microscopic bodies produced according to section A above, showed that the vast majority were small unilamellar structures slightly contaminated by larger multilamellar structures (i.e. Liposomes). The majority of the lipid discs were in the size range 50 to 100 nm.

B. Examination in the same manner of the influenza subunit preparation used in Example 1C above revealed only the typical star and cartwheel forms associated with haemagglutinin and neuraminidase subunits. No trace of viral membrane could be found.

F. Examination in the same manner of the preparation resulting from the procedure described in section C above, showed that the majority of subunits were now arranged on the surface of the unilamellar bodies to give an appearance very like that of influenza virus. In the majority of microscopic bodies, the haemagluttinin subunits were the prominent feature, but in some areas the attachment of neuraminidase subunits could be seen. In further examination of these microscopic bodies by immune electro microscopy, the addition of hyperimmune influenza A antiserum aggregated the bodies into large complexes.

EXAMPLE 2

A. Preparation of Ethanol Microvesicles

Egg lecithin (30 mg) in chloroform was dried in a rotary evaporator for 1½ hours in partial vacuum. Ethanol (2 ml) was added to dissolve the dried lipid and the resulting solution taken up into a 2 ml syringe fitted with a 27 gauge hypodermic needle.

Potassium chloride solution (30 ml, 0.16 M) was gassed with nitrogen for 1 hour and the ethanolic solution of lecithin syringed rapidly through a 27 gauge needle into the potassium chloride solution.

The resulting liposome preparation was concentrated by ultra-filtration to approximately 3 ml using an Amicon model 52 ultra-filtration cell fitted with a PM 30 membrane. (Lit. ref. B.B. Acta, 298 (1973) 1015–1019).

B. Preparation of Virosomes

Ethanol microvesicles prepared by the method described in Example 2A, were mixed with an equal volume of influenza virus X31 sub-units (250 µg/ml) and lightly sonicated.

EXAMPLE 3

Preparation of Multilamellar Virosomes

Dicetyl phosphate (2.5 mg) and lecithin (22.5 mg) were dissolved in chloroform (approximately 50 ml). The solution was evaporated to dryness on a Buchi evaporator under a slight vacuum. Influenza virus X31 antigen (5 ml) preparation in PBS was added to the contents of the flask and the flask was agitated manually and mechanically until the lipid was suspended in the fluid. The mixture was transferred to a vial and subjected to ultrasound for 1.5 minutes using a 1 cm probe and 8 µ amplitude.

EXAMPLE 4

Mouse Protection Test

The virosome preparations of Examples 2 and 3 were assayed for protection.

Twenty mice were divided into four groups of five, and the first group injected intra-peritonealliy with the viral subunits used in Examples 2 and 3 above at a dose of 42 μg/0.25 ml. The second and third groups were similarly dosed with the virosomes produced as described in Examples 2 and 3 respectively each group receiving 42 μg per 0.25 ml. The fourth group was unimmunised.

Ten days later the mice were challenged with live virus of the same strain and the lungs harvested two days later. The lungs were homogenised and sonicated to release any virus present and the suspensions assayed by allantois-on-shell cultures, as described by Fazekas de St. Groth and White (1958) Journal of Hygiene 56 151, (1958).

The results are shown in Table 1 which shows the relative effectiveness of the various treatments in providing protection against virus infection. A consideration of the virus lung titration of the unilamellar virosome shows that in only one mouse of the five mice immunized with such a virosome was any virus detected in the tests whereas in the case of the multilamellar virosome the tests showed substantial residual virus in three of the mice treated with such a virosome, indicating that the protection afforded by "unilamellar virosomes" is substantially greater than that produced by either "multilamellar virosomes" or the unbound antigen.

TABLE 1

| Antigen | Type of Microvesicle | Dose | Mouse No. | Log$_{10}$ Virus Lung Titration MEAN | AVERAGE |
|---|---|---|---|---|---|
| 45 μg X31 subunits on alcohol liposomes (from Example 2) | Unilamellar | 42 μg in 0.25 ml. | 1<br>2<br>3 | −1.75<br>−1.75<br>−1.75<br>−1.75<br>−2.25 | −1.85<br>±0.22 |
| 42 μg X31 on subunits on lightly sonicated lecithin/DCP liposomes (from Example 3) | Multilamellar | 42 μg in 0.25 ml. | 11<br>12<br>13<br>14<br>15 | −4.00<br>−1.75<br>−1.75<br>−4.31<br>−4.31 | −3.22<br>±1.35 |
| 42 μg X31 subunits in phosphate buffered saline (PBS) | None | 42 μg in 0.25 ml. | 16<br>17<br>18<br>19<br>20 | −3.31<br>−2.63<br>−3.88<br>−3.13<br>−1.81 | −2.95<br>±0.78 |
| Unimmunized | None | — | 21<br>22<br>23<br>24<br>25 | −4.06<br>−4.50<br>−4.50<br>−4.56<br>−4.50 | −4.42<br>±0.78 |

EXAMPLE 5

Parenteral Solution

| | |
|---|---|
| Lecithin/dicetylphosphate (9:1, w/w) | 1 mg |
| Influenza virus X31 protein subunits | 50 μg |
| Sodium merthiolate | 40 μ |
| Phosphate buffered saline (pH 7.2) | 0.2 ml |
| Phosphate buffered saline contains: | |
| Sodium chloride | 10 g/liter |
| Potassium chloride | 0.25 g/liter |
| Potassium dihydrogen phosphate | 0.25 g/liter |
| Disodium hydrogen phosphate | 1.4375 g/liter |

What is claimed is:

1. An antigenic virosome preparation containing a plurality of microvesicles which microvesicles are unilamellar bodies having a single lipid bilayer upon the exterior surface of which is bound by hydrophobic bonding an antigenic protein, said antigenic protein being a hemagglutinin and neuraminidase sub-unit of a protective surface antigen derived from a myxovirus and having a hydrophobic region.

2. An antigenic virosome preparation as claimed in claim 1 wherein the walls of the microvesicles contain lecithin.

3. An antigenic virosome preparation as claimed in claim 1 wherein the microvesicles contain cholesterol as a strengthener.

4. An antigenic virosome preparation as claimed in claim 1 wherein the virus is an influenza virus.

5. An antigenic virosome preparation as claimed in claim 1 wherein the microvesicles encapsulate an additional adjuvant.

6. An antigenic virosome preparation as claimed in claim 1 wherein the microvesicles are in the size range of 20 nm to 100 nm.

7. A pharmaceutical formulation which comprises an antigenic virosome preparation containing a plurality of microvesicles, which microvesicles are unilamellar bodies having a single lipid bilayer upon the exterior surface of which is bound by hydrophobic bonding an antigenic protein, said antigenic protein being a hemagglutinin and neuramidinase sub-unit of a protective surface antigen derived from a myxovirus and having a hydrophobic region, in association with an acceptable carrier therefor.

8. A formulation according to claim 7 wherein the carrier comprises a liquid.

9. A formulation according to claim 7 in unit dosage form.

10. A formulation according to claim 7 which is suitable for administration by a route selected from nasal and parenteral.

11. A method for inducing antibody formation in a mammal, which comprises the administration to the mammal of a non-toxic antibody stimulating amount of an antigenic virosome preparation containing a plurality of microvesicles, which microvesicles are unilamellar bodies having a single lipid bilayer upon the exterior surface of which is bound by hydrophobic bonding an antigenic protein a hemagglutinin and neuraminidase sub-unit of a protective surface antigen derived from a myxovirus and having a hydrophobic region.

12. A method for the prophylaxis of influenza in a mammal which comprises the administration to the mammal of a non-toxic, prophylactic amount of an antigenic virosome preparation containing a plurality of microvesicles, which microvesicles are unilamellar bodies having a single lipid bilayer upon the exterior surface of which is bound by hydrophobic bonding an antigenic protein having a hydrophobic region and a hemagglutinin and neuraminidase sub-unit of a protective surface antigen derived from an influenza virus.

* * * * *

UNITED STATES PATENT AND TRADEMARK OFFICE
CERTIFICATE OF CORRECTION

PATENT NO. : 4,148,876

DATED : APRIL 10, 1979

INVENTOR(S) : JUNE D. ALMEIDA ET AL

It is certified that error appears in the above-identified patent and that said Letters Patent are hereby corrected as shown below:

FOREIGN APPLICATION PRIORITY DATA

Sept. 29, 1975[G.B.]  United Kingdom..........39857/75

Signed and Sealed this

Twenty-third Day of October 1979

[SEAL]

Attest:

RUTH C. MASON
Attesting Officer

LUTRELLE F. PARKER
Acting Commissioner of Patents and Trademarks